United States Patent [19]

Sisto et al.

[11] Patent Number: 4,522,752

[45] Date of Patent: Jun. 11, 1985

[54] RETRO-INVERSO ANALOGUES OF THE BRADYKININ POTENTIATING PEPTIDE BPP$_{5a}$ AND METHODS FOR THEIR PREPARATION

[75] Inventors: Alessandro Sisto, Rome; Antonio S. Verdini, Monterotondo; Antonino Virdia, Rome, all of Italy

[73] Assignee: E.N.I. Ente Nazionale Idrocarburi, Rome, Italy

[21] Appl. No.: 608,985

[22] Filed: May 10, 1984

[30] Foreign Application Priority Data

May 13, 1983 [IT] Italy .................. 21083 A/83

[51] Int. Cl.³ ............................................ C07C 103/52
[52] U.S. Cl. ............................................... 260/112.5 R
[58] Field of Search ............................... 260/112.5 R

[56] References Cited

PUBLICATIONS

Experientia 32/12, (1976), 1503–1504.

European Journal of Pharmacology 79, (1982), 155–158.

*Primary Examiner*—Delbert R. Phillips
*Attorney, Agent, or Firm*—Hedman, Gibson, Costigan & Hoare

[57] ABSTRACT

This invention relates to new retro-inverso peptides and peptide derivatives in the form of analogues of the bradykinin potentiating peptide (BPP$_{5a}$), which are pharmacologically active, have long in vivo life and are useful as antihypertensives and diagnostic drugs, their general formula (I) being

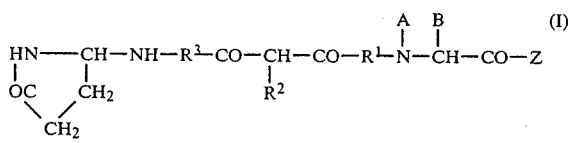

5 Claims, No Drawings

RETRO-INVERSO ANALOGUES OF THE BRADYKININ POTENTIATING PEPTIDE BPP$_{5a}$ AND METHODS FOR THEIR PREPARATION

DESCRIPTION

The renin-angiotensin- aldosterone system has been recently recognised as one of the factors of primary importance in determining the onset of hypertension.

The action of the renin enzyme on a pseudoglobulin of the blood plasma produces a peptide, angiotensin I, which is converted into the octapeptide angiotensin II by the angiotensin conversion enzyme. Angiotensin II exerts a powerful vasoconstricting action which produces an increase in blood pressure.

The angiotensin conversion enzyme is also responsible for inactivating the bradykinin, a nonapeptide with powerful hypotensive action. The net result of this double action is an increase in arterial blood pressure.

Compounds which inhibit the angiotensin conversion enzyme could be useful as antihypertensive agents in the treatment of renal hypertension, malign hypertension and essential hypertension.

These inhibitors could also be used as diagnostic drugs in studies for determining the degree of involvement of the renin-angiotensin system in the onset and maintenance of hypertensive states. This would be of great importance in choosing the most appropriate therapeutic treatment [Tifft, C. P. et al., Ann. Int. Med., 90, 43 (1979)]. Peptides which potentiate bradykinin activity and inhibit the angiotensin conversion enzyme [Ferreira S. M.; Br. J. Pharmacol., 24, 163 (1965); Ferreira S. M. et al., Biochemistry 9, 2583 (1970); Ondetti M. A. et al., Biochemistry 10, 4033 (1971)] [Ferreira S. M. et al., Nature (London), 225, 379 (1970)] have been isolated from the venom of the Bothrops Jararaca snake.

The pentapeptide Glp-Lys-Trp-Ala-Pro (BPP$_{5a}$) Greene L. J. et al., Advan. Exp. Biol., 8, 81 (1970); Stewart J. M. et al., Biochem. Pharmacol., 20, 1557 (1971)], which has been found to be the most potent inhibitor of the angiotensin conversion enzyme in vitro [Cheung H. S. et al., Biochem. Biophsy. Acta, 293, 451 (1973); Ondetti M. A. et al., Chemistry and Biology of Peptides, Ed. J. Meienhofer (Ann Arbor Science Publishers, Ann Arbor 1972) p. 525], causes a regression of reno-vascular hypertension induced experimentally in the rat [Krieger E. M. et al., Lancet, 1, 269 (1971)], potentiates in vivo the activity of bradykinin injected directly into the coronary arteries [Bassenge E. et al., Vasopeptides, Chemistry, Pharmacology and Pathophysiology, Ed. Nathan Back & F. Sicuteri (1972) 251], and when injected directly into the brain inhibits the hypertensive and tachycardiac action of angiotensin I mediated by the central nervous system [Solomon T. A. et al., J. Pharm. Sci., 63, 511 (1974); Vollmer R. R. et al., Eur. J. Pharmacology 45. 117 (1977)]. BPP$_{5a}$ behaves as a "mixed inhibitor", competitive and non-competitive, in accordance with the hypothesis that it can recognise two conversion enzyme receptor sites: in one it bonds with the terminal C tripeptide and in the other with the terminal N dipeptide, Cushman D. W. et al., Experientia, 29 (8), 1032 (1973) and cited references.

Structure-function studies carried out on a series of BPP$_{5a}$ analogues have shown that:

(a) only the terminal C tripeptide bonds to the same active site of the enzyme to which the entire decapeptide angiotensin I bonds;

(b) the enzymatic activity is expressed only when the terminal C carboxyl is free;

(c) the enzyme does not hydrolyse peptides containing a dicarboxylic amino acid residue in position 5, or an imino acid, such as proline, in position 4;

(d) substrates containing a tryptophan or a phenylalanine in position 3 bond to the enzyme with greater affinity than substrates which have different residues in the same position;

(e) the introduction of amino acids with D configuration in position 3 causes loss of the inhibitory activity.

As biological in vivo stability is one of the essential requirements for the use of peptide inhibitors as drugs, the extreme lability of BPP$_{5a}$ to the angiotensin conversion enzyme has prejudiced its widespread pharmacological and clinincal use. In this respect, 15 minutes of preincubation with the enzyme are sufficient for it to completely lose its inhibitory activity [Ondetti M. A. et al., Annual Reports in Medicinal Chemistry Chap. 9, 82 (1978); Ondetti M. A. et al., Drug Action and Design: Mechanism Based Enzyme Inhibitors, Ed. Kalman, by Elsevier North Holland Inc., p. 271 (1979); Cushman D. W. et al., Progress in Medicinal Chemistry, 17, Chap. 2, 42 (1980) and cited references].

For this reason, of the peptides extracted from the venom of the Bothrops Jararaca snake, virtually only BPP$_{9a}$, a nonapeptide of Clp-Trp-Pro-Arg-Pro-Gln-Ile-Pro-Pro sequence (teprotide) which is more stable to peptidase action, has been used in pharmacological and clinical studies [Soffer R. L. et al., Progress in Cardiovascular diseases, vol XXI, 3, 167 (1968); Ondetti M. A. et al., J. Med. Chemistry 24 (4) 355 (1981); Rubin B et al., Progress in Cardiovascular Diseases vol XXI, 3, 183 (1978) and cited references; Cushman D. W. et al., Progress in Cardiovascular Diseases vol XXI. 3, 176 (1978); Hulthen L et al., Acta Med. Scan., 204, 499 (1978); Castaner J., Drug of the Future vol III, 1, 62 (1978); Martin L. C. et al., Biochem. J., 184, 713 (1979); Depierre D. et al., Enzyme 24, 362 (1979)].

Teprotide has proved a powerful antihypertensive, which has also been clinically experimented on man where it has given excellent results, even in malign hypertension [H. Gavras H. R. Brummer, J. H. Laragh, J. E. Scaley, I. Gavras and R. A. Vukovich, New. Engl. J. Med, 291, 817 (1974); J. Johnson, W. D. Black, R. A. Vukovich, F. E. Hatch, B. I. Friedman, C. F. Blackwell, A. N. Shenouda, L. Share, R. E. Shade, S. R. Acchiardo and E. E. Muirhead, Clin. Sci. Mol. Med., 48, 53 (1975)]. The main defect of teprotide is the need for intravenous administration because it is inactive orally. It is therefore a drug which is very useful, but only for diagnostic purposes.

Compounds which are active when administered orally and are effective as antihypertensives both in experimental hypertension and in human hypertension have been recently developed by the researchers of Squibb (captopril) and of Merck, Sharp and Dohme (MK-421) on the basis of a model of the active site of the conversion enzyme [M. A. Ondetti, B. Rubin, D. W. Cushman, Science, 196 441 (1977); A. A. Patchett et al., Nature, 288, 280 (1980)]. Clinical studies on the compound MK-421 are currently underway [H. Gavras et al., Lancet, 2, 543 (1981); J. Biollaz et al., Clin. Pharmac. Ther. 29, 665 (1981); D. B. Brunner et al., Brit. J. Clin. Pharmac. , II, 461 (1981)], whereas the use of captopril in therapy has been approved in numerous countries for treating hypertension and refractory cardiac congestion states, in spite of the numerous side effects encountered during the clinical tests, such as cutaneous rashes, fever, allergic dermatitis, leukopenia, agranulocytosis and proteinurea deriving from nephrosis or glomerulopathy [Editorial, Lancet, 2, 129 (1980)].

The presence of toxic effects resulting from the taking of captopril has led us to reconsider the problem of developing peptide inhibitors of the renin-angiotensin system which can be used therapeutically. Both teprotide and saralasin (an angiotensin II antagonist peptide which is active on intravenous injection) are known to be practically free from toxic effects, even if not as effective as captopril [D. H. P. Streeten and G. H. Anderson, Kidney Intern.; 15, S-44, S-52 (1979); D. B. Cose et al., Am. J. Med. 60, 825 (1976); J. H. Keim et al., New Engl. J. Med., 295, 1175 (1976); F. G. Dunn et al., New Engl. J. Med. 295, 605 (1976)].

We therefore decided to determine the synthesis of $BPP_{5a}$ analogues, of which the peptide skeleton was modified in such a manner as to be stable to the in vivo demolishing action of peptidase, but without losing the inhibitory properties towards the conversion enzyme. In order to obtain adequate in vivo stabilisation of the peptide sequences of the analogues, we have found it extremely advantageous to apply the peptide bond retro-inversion method, and this forms part of the present invention.

We have therefore suitably inverted two peptide bonds of the $BPP_{5a}$ sequence which are susceptible to peptidase hydrolytic action, i.e. the bonds between the 1,2 and 2,3 amino acid residues.

The three-dimensional orientation of the peptide side chains is preserved by this modification, and by allowing correct binding to the active site of the conversion enzyme partly maintains or potentiates the biological activity of the analogue. The inversion of two peptide bonds of the sequence requires the chemical modification of the two amino acid residues in position 1 and 3 and the simultaneous inversion of the chirality of the residue 2. In particular, the pyroglutamic acid residue is transformed into a gem-diamino residue of structure:

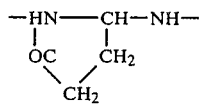

and the residue in position 3 is transformed into a residue of malonyl or 2-substituted malonyl type of general structure $-OC-CHR^2-CO-$ where $R^2$ represents the side chain of the amino acid residues present in the chains of natural polypeptides or a synthesis analogue thereof [Goodman M et al., Acc. Chem. Res., 12, 1 (1979)].

Incorporating malonyl or 2-substituted malonyl residues into the peptide skeleton does not present particular problems, whereas incorporating gem-diamino residues generally requires special and delicate synthesis manipulations [Goodman M. et al., Perspectives in Peptide Chemistry, Ed. Eberle A., Geiger R., Wieland T., Karger, Basel, p. 283 (1980)].

We have recently established a method which makes it possible to very easily introduce a gem-diamino residue into a peptide skeleton without special tedious chemical manipulations, by using 1,1-bis-(trifluoroacetoxy)-iodobenzene. This new reagent had been previously used for directly converting primary amides of simple structure into amines under extremely mild reaction conditions, without the need for isolating or recovering the intermediate isocyanate [Radhakrisna A. S. et al., J. Org. Chem. 44, 1746 (1979)].

Our method, described in copending patent applications in the name of the present applicant, is easily applied to the direct conversion of primary peptide amides, protected at the terminal $NH_2$, into the corresponding trifluoroacetic acid salts of N-monoacylated gem-diamino derivatives.

We have thus been able to very easily synthesise, both in the homogeneous phase and on insoluble polyamide matrices, partially retroinverted analogues of biologically active peptides as described in the copending patent applications in the name of the present applicant.

The retro-inverso peptides according to the present invention are those of general formula (I):

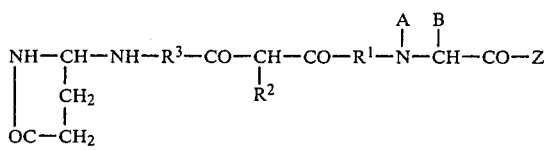

where $R^3$ represents an amino acid residue of D configuration; $R^2$ represents the side chain of one of the amino acid residues present in the chains of natural peptides or systhesis analogues thereof; $R^1$ represents an amino acid residue of L configuration; A represents a hydrogen atom, an alkyl, aryl, hydroxyalkylene or arylalkylene group; B represents a hydrogen atom or an alkyl, aryl, arylalkylene, hydroxyalkylene, guanidinylalkylene, aminoalkylene, alkyloxyalkylene, acylaminoalkylene, imidazoylalkylene, indolylalkylene, mercaptoalkylene, alkylmercaptoalkylene, carbamoylalkylene, carboxyalkylene, alkylcarbamoylalkylene or alkyloxycarbonylalkylene group.

A and B taken together can be a $-(CH_2)_m-$ residue closed to form a ring on the nitrogen and carbon atoms to which they are joined, where m equals 2, 3 or 4.

One carbon atom of the $-(CH_2)_m-$ bridge can be joined directly to a hydroxyl, $-O-$benzyl or $-S-$phenyl group; or A and B, taken together, are joined together by a bridge of carbon atoms containing an olefin bond which completes a 5 or 6 atom ring by way of the nitrogen and carbon to which they are joined; or A and B, taken together, are joined together by a $-CH_2-S-(CH_2)_q-$ or $-CH_2-O-(CH_2)_q-$ bridge which completes a 5 or 6 atom ring by way of the nitrogen and carbon to which they are joined, where q is 1 or 2;

B can also be bonded to the carbon atom by unsaturated bonds;

Z represents a hydroxyl, hydroxyalkyl or amino group.

The following abbreviations are used in the synthesis descriptions given hereinafter:

Boc=tert.butyloxycarbonyl; Z=benzyloxycarbonyl; EtO=ethyl ester; O'Bu=tert.butyl ester; DCC=N, N'-dicyclohexylcarbodiimide; DCU=dicyclohexylurea; HOB'=N-hydroxybenzotriazole; DMF=N,N-dimethylformamide; THF=tetrahydrofuran; NMM=N-methylmorpholine; MeOH=methanol; EtOH=ethanol; MeCN=acetonitrile; EtOAc=ethyl acetate; Et2O=ethyl ether; TFA=trifluoroacetic acid; BTI=1,1-bis-(trifluoroacetoxy)-iodobenzene.

A peptide of general formula (I) is synthesised by condensing the fragment of general formula (II)

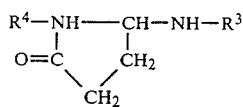

where $R^4$ can be a hydrogen atom, an alkyloxycarbonyl or arylalkyloxycarbonyl and $R^3$ an amino acid residue of D configuration conveniently protected at the amino function and, if present, at the side chain function by the temporary protector groups used in peptide synthesis, with a peptide fragment of general formula (III):

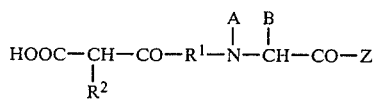

where $R^1$, $R^2$, A, B and Z have the meaning given heretofore, and in which the amino, hydroxyl, carboxyl, carboxyamido, indole, imidazole, guanidino, mercaptan and sulphhydryl functions, if present in $R^1$, $R^2$, A, B or Z, are suitably protected, the condensation being induced generally by DCC and HOB$^t$.

Synthesis of the fragments of general formula (II) and (III) is conducted by using the peptide synthesis methods described for example in Bodanszki M. and Ondetti M. A., Peptide Synthesis, Interscience, New York, 1976; and The Peptides, vol 1, Gross E. and Meienhofer L., Editors, Academic Press, New York, 1979.

After completing the condensation reaction and the removal of the temporary protector groups, the peptides are obtained by known peptide isolation processes such as extraction, counter-current distribution, precipitation, crystallisation and chromatography.

Product identity is demonstrated by nuclear magnetic resonance spectroscopic analysis.

Product purity is checked by reverse phase high pressure chromatography analysis (RP-HPLC) using the following eluent systems:

$H_2O$/MeCN, TFA 0.1% in aqueous/MeCN solution; and silica gel thin layer chromatography analysis using the following eluent systems: n-butanol:acetic acid:water (4:1:1); chloroform:methanol:acetic acid (85:10:5); n-butanol:isopropanol:1N $NH_4OH$ in water:ethyl acetate (1:1:5:1), organic phase.

The inhibition of the angiotensin conversion enzyme by the compounds of general formula (I) is measured in vitro by the enzyme isolated from rabbit lungs by the method of Cushman and Cheung [Biochem. Pharmacol., 20, 1637 (1971)].

Table 1 shows the values of $I_{50}(\mu M)$ obtained on using the retro-inverso analogues claimed as original products in the present patent, and the unmodified analogues which are used for comparison purposes.

TABLE 1

| Peptide | $I_{50}(\mu M)$ |
| --- | --- |
| Glp—Lys—Phe—Ala—Pro | 0.13 (lit. = 0.07) |
| Glp—Lys—Phe—Ala—Hyp(OBz) | 0.11 |
| Glp—Lys—Phe—Ala—Pro(4-allo-SPh) | 0.06 |
| gGlp—D-Lys—mPhe—Ala—Pro | 85 |
| gGlp—D-Lys—mPhe—Ala—Hyp(OBz) | 40 |
| gGlp—D-Lys—mPhe—Ala—Pro(4-allo-SPh) | 2 |

The subject matter and object of the invention will be more apparent from reading the following examples which are given as illustration only and must in no way be considered as limitative of the invention itself.

Synthesis of gem-pyroglutamyl-D-lysyl-(R,S)-malonyl-(2-benzyl)-alanyl-proline. gGlp-D-Lys-(R,S)-mPhe-Ala-Pro Synthesis of pyroglutamyl amide. Glp-NH$_2$ 1.0 equivalent of Glp is dissolved in anhydrous DMF and 1.2 equivalents of $HOBt.NH_3$ dissolved in DMF and 1.1 equivalents of DCC dissolved in DMF are added to the solution cooled to 0° C. under strong agitation. The ice bath is removed after one hour, and the reaction mixture is left under agitation for a further hour. The precipitated DCU is filtered off and washed with DMF. The solution and the DMF used for washing are added together and evaporated to dryness under reduced pressure. The residue is triturated with EtOAc. The product is filtered off, dissolved in MeOH and precipitated by adding $Et_2O$. The precipitate is filtered off, washed with $Et_2O$ and dried.

M.P.=166°–168° C.

$[\alpha]_{25}^{589} = -42.0°$ (c=2.0 in $H_2O$)

Chromatographic analysis (t.l.c. and h.p.l.c.) shows no presence of impurities, and the $^1H$ n.m.r. spectrum confirms the molecular structure.

Synthesis of the trifluoroacetate of gem-diamino-pyroglutamic acid. gGlp.TFA 1.0 equivalent of Glp-NH$_2$ are suspended in a MeCN-$H_2O$ (3:2) solution, and 1.2 equivalents of BTI dissolved in acetonitrile are added to the suspension at ambient temperature under forced agitation.

After 3 hours, and having checked the disappearance of the Glp-NH$_2$, the reaction is suspended by evaporating the solvent to dryness. The residue is taken up in EtOAc. The precipitate obtained is filtered off, washed with $Et_2O$ and dried. M.P. 125°–127° C. (decomp.)

$[\alpha]_{25}^{589} = 0.4°$ (C=1.0 in MeOH)

Chromatographic analysis (t.l.c. and h.p.l.c.) shows no presence of impurities, and the $^1H$ n.m.r. spectrum confirms the molecular structure.

Synthesis of $N^\alpha$-tert.butyloxycarbonyl-D-lysyl-($N^\epsilon$-trifluoroacetyl)-gem-pyroglutanic acid. Boc-D-Lys($N^\epsilon$-TFA)-gGlp 10 equivalents of Boc-D-Lys($N^\epsilon$-TFA) are dissolved in $CH_2Cl_2$, and 1.2 equivalents of HOBt dissolved in DMF and 1.1 equivalents of DCC dissolved in $CH_2Cl_2$ are added to the solution cooled to 0° C. and under strong agitation.

The ice bath is removed after 30 minutes, and the reaction mixture is left under agitation for a further 30 minutes. A solution of 1.1 equivalents of gGlp.TFA and 1.1 equivalents of NMM is then added. After one hour the reaction mixture is filtered, the DCU is washed with $CH_2Cl_2$, and the solution evaporated to dryness. The resultant oil is taken up in EtOAc and extracted with 5% sodium bicarbonate and a saturated solution of sodium chloride. The organic solution is dried over magnesium sulphate, and the solvent is then evaporated under reduced pressure. The solid residue is triturated with ethyl ether, filtered and dried.

M.P.=133°–134° C.

$[\alpha]_{25}^{589} = 2.9°$ (c=1.0 in MeOH)

Chromatographic analysis (t.l.c. and h.p.l.c.) shows no trace of impurities, and the $^1$H n.m.r. spectrum confirms the molecular structure.

Synthesis of tert.butyloxycarbonyl-alanyl-proline methyl ester. Boc-Ala-Pro-OMe 1.1 equivalents of Boc-Ala are dissolved in CH$_2$Cl$_2$, and 1.2 equivalents of HOBt dissolved in DMF and 1.1 equivalents of DCC dissolved in CH$_2$Cl$_2$ are added to the solution cooled to 0° C. and under strong agitation.

The mixture is left under agitation for 30 minutes at 0° C. and for a further 30 minutes at ambient temperature. A solution of 1.0 equivalent of HCl.Pro-OMe and 1.0 equivalent of NMM dissolved in CH$_2$Cl$_2$ is then added. After 2 hours, and having checked the disappearance of the HCl.Pro-OMe, the reaction mixture is separated from the precipitated DCU and evaporated to dryness.

The oily residue is taken up in EtOAc and extracted with 5% sodium bicarbonate, water, 0.1N HCl and water. The organic solution is dried over magnesium sulphate.

The solvent is then evaporated to obtain the product in the form of a slightly yellow-coloured oil. The crude product is chromatographed on silica using 0.5% MeOH in CHCl$_3$ as eluent.

On evaporating the collected fractions, the product is obtained as a colourless oil. Chromatographic analysis (t.l.c. and h.p.l.c.) shows no trace of impurities, and the $^1$H n.m.r. spectrum confirms the molecular structure.

Synthesis of the mixed tert.butyl and ethyl ester of (R,S)-2-benzylmalonic acid. EtO-mPhe-OBu$^t$ 0.1 equivalents of concentrated H$_2$SO$_4$ are added to 1.0 equivalent of EtO-mPhe-OH dissolved in anhydrous CH$_2$Cl$_2$. The solution is saturated with isobutylene and agitated for 65 hours at ambient temperature. The reaction mixture is extracted with 5% sodium bicarbonate and water. The product is obtained as a transparent oil on evaporating the solvent.

The product is chromatographically pure, and its structure is confirmed by the $^1$H n.m.r. spectrum.

Synthesis of the tert.butyl ester of (R,S)-2-benzylmalonic acid. HO-mPhe-OBu$^t$ 1.0 equivalent of KOH in EtOH are added drop by drop over two hours to 1.0 equivalent of EtO-mPhe-OBu$^t$ dissolved in EtOH. The reaction mixture is evaporated to dryness after 16 hours. The residue is taken up in water and extracted with Et$_2$O. The aqueous phase is then acidified with 1N HCl to pH 3, and extracted with EtOAc. The organic extracts are added together, extracted with a saturated sodium chloride solution and dried over magnesium sulphate. The product is obtained as a transparent oil on evaporating the solvent under reduced pressure.

Chromatographic analysis (t.l.c. and h.p.l.c.) shows no presence of impurities, and the $^1$H n.m.r. spectrum confirms the molecular structure.

Synthesis of the tert.butyl ester of (R,S)-malonyl-(2-benzyl)-alanyl-proline methyl ester. Bu$^t$O-mPhe-Ala-Pro-OMe 1.0 equivalent of Bu$^t$O-mPhe are dissolved in CH$_2$Cl$_2$, and 1.2 equivalents of HOBt dissolved in DMF and 1.1 equivalents of DCC dissolved in CH$_2$Cl$_2$ added to the solution cooled to 0° C. and under strong agitation. The ice bath is removed after 30 minutes and the mixture left under agitation for 30 minutes at ambient temperature. A solution of 1.1 equivalents of HCl.Ala-Pro-OMe (obtained by removing the tert.butyloxycarbonyl from Boc-Ala-Pro-OMe with 4.5N HCl in EtOAc) and 1.1 equivalents of NMM dissolved in CH$_2$Cl$_2$ is then added.

After two hours, and having checked the disappearance of the Bu$^t$O-mPhe, the reaction mixture is filtered and evaporated to dryness. The solid residue is taken up in EtOAc and extracted with 5% sodium bicarbonate, water, 0.2N HCl and water. The organic solution is dried over magnesium sulphate.

The solvent is then evaporated to obtain the product as a very dense oil. Chromatographic analysis (t.l.c. and h.p.l.c.) shows no trace of impurities and the $^1$H n.m.r. spectrum confirms the molecular structure.

Synthesis of (R,S)-malonyl-(2-benzyl)-alanyl-proline methyl ester. (R,S)-mPhe-Ala-Pro-OMe 1.0 equivalent of Bu$^t$O-mPhe-Ala-Pro-OMe are dissolved in a 4.5N solution of HCl in EtOAc. On checking the disappearance of the starting substance, the solvent is evaporated to dryness. The residue is taken up several times in MeOH and evaporated to dryness. The product is obtained in the form of a very dense colourless oil. Chromatographic analysis (t.l.c. and h.p.l.c.) shows no trace of impurities, and the $^1$H n.m.r. spectrum confirms the molecular structure.

Synthesis of gem-Pyroglutamyl-D-lysyl-(N$^\epsilon$-trifluoroacetyl)-(R,S)-malonyl-(2-benzyl)-alanyl-proline methyl ester. gGlp-DLys(N$^\epsilon$-TFA)-(R,S)-mPhe-Ala-Pro-OMe 1.1 equivalents of gGlp-DLys(N$^\epsilon$-TFA).HCl (obtained by removing the tert,butyloxycarbonyl from gGlp-DLys(N$^\epsilon$-TFA)-Boc with 4.5N HCl in EtOAc), 1.1 equivalents of NMM, 1.2 equivalents of HOBt and finally 1.1 equivalents of DCC are added to the cooled solution of 1.0 equivalent of (R,S)-mPhe-Ala-Pro-OMe in DMF. The ice bath is removed after one hour, and the reaction mixture is left under agitation for a further 2.5 hours.

After checking the disappearance of the (R,S)-mPhe-Ala-Pro-OMe, the DCU precipitate is filtered off and washed with DMF. The solution and the DMF used for washing are added together and evaporated to dryness under reduced pressure. The residue is dissolved in EtOAc and extracted with 5% sodium bicarbonate and water. The organic solution is dried over magnesium sulphate.

The solvent is evaporated and the residue is triturated with Et$_2$O/hexane, filtered and dried.

M.P.=83°-85° C. (dec.); $[\alpha]_{25}^{589} = -10.0°$ (c=1.0 in MeOH)

Chromatographic analysis (t.l.c. and h.p.l.c.) shows no trace of impurities and the $^1$H n.m.r. spectrum confirms the molecular structure.

Synthesis of gem-pyroglutamyl-D-lysyl-(R,S)-malonyl-(2-benzyl)-alanyl-proline. gGlp-DLys(R,S)mPhe-Ala-Pro 1.0 equivalent of gGlp-D-Lys(N$^\epsilon$-TFA)-(R,S)-mPhe-Ala-Pro-OMe are dissolved in a MeOH/pyridine (1:1 v/v) mixture, and 5 equivalents of NaCl in aqueous solution are added to the solution which has been cooled to 0° C. and is under strong agitation. After 4 hours, and having checked the disappearance of the starting substance, 5 equivalents of HCl in aqueous solution are added. After diluting with water, the reaction mixture is evaporated to dryness. It is taken up in water and lyophilised. The product is isolated by high pressure preparative liquid chromatography with the stationary phase constituted by Lichroprep ® RP-18, 25-40 μ (Merck), using 0.1% TFA and 18% MeCN in water as eluent. The fractions containing the product are added together, the MeCN is evaporated and the required product obtained by lyophilisation.

M.P. = 168°-170° C.

$[\alpha]_{25}^{579} = -33.0°$ (C = 1.12 in $H_2O$)

Chromatographic analysis shows no presence of impurities, and the $^1H$ n.m.r. spectrum confirms the molecular structure.

Synthesis of gem-pyroglutamyl-D-lysyl-(R,S)-malonyl-(2-benzyl-)alanyl-(4-benzyloxy)-proline. gGlp-D-Lys-(R,S)-mPhe-Ala-Hyp(OBz)

Synthesis of tert.butyloxycarbonyl-alanyl-(4-benzyloxy)-proline methyl ester. Boc-Ala-Hyp-(OBz)OMe 1.1 equivalents of Boc-Ala are dissolved in $CH_2Cl_2$, and 1.2 equivalents of HOBt dissolved in DMF and 1.1 equivalents of DCC dissolved in $CH_2Cl_2$ are added to the solution cooled to 0° C.

The ice bath is removed after 20 minutes, and a solution of 1.0 equivalent of HCl.Hyp(OBz)-OMe [prepared by a known process: S. Sakakibara et al., Biochim. Biophys. Acta 303, 198 (1973)] and 1.1 equivalents of NMM dissolved in $CH_2Cl_2$ are added. After 2 hours, and having checked the disappearance of HCl.Hyp(OBz)-OMe, the reaction mixture is filtered from the precipitated DCU and evaporated to dryness.

The solid residue is taken up in EtOAc.

After remaining at −20° C. for one hour, the solution is filtered and the precipitate washed with cold EtOAc. The solution and the EtOAc used for washing are added together and evaporated to dryness, the residue being crystallised from EtOAc/petroleum ether.

M.P. = 92°-93° C.

$[\alpha]_{25}^{579} = -47.6°$ (C = 1.0 in $CHCl_3$)

Chromatographic analysis (t.l.c. and h.p.l.c.) shows no presence of impurities and the $^1H$ n.m.r. spectrum confirms the molecular structure.

Synthesis of the tert.butyl ester of (R,S)-malonyl-(2-benzyl)-alanyl-(4-benzyloxy)-proline methyl ester. Bu$^t$O(R,S)-mPhe-Ala-Hyp-(OBz)OMe.

1.1 equivalents of Bu$^t$O(R,S)mPhe are dissolved in $CH_2Cl_2$, and 1.2 equivalents of HOBt dissolved in DMF and 1.1 equivalents of DCC dissolved in $CH_2Cl_2$ are added to the solution cooled to 0° C. and under strong agitation. The ice bath is removed after 30 minutes, and the mixture left under agitation for a further 30 minutes at ambient temperature. A solution of 1.1 equivalents of HCl.Ala-Hyp-(OBz)-OMe (obtained by removing tert.butyloxycarbonyl from Boc-Ala-Hyp-(OBz)Ome with 4.5N HCl in EtOAc) and 1.1 equivalents of NMM in $CH_2Cl_2$ is added.

After 2 hours, having checked the disappearance of the Bu$^t$OmPhe, the reaction mixture is filtered and evaporated to dryness. The oily residue is taken up in EtOAc and extracted with 5% sodium bicarbonate, water, 0.1N HCl, and water. The organic solution is dried over magnesium sulphate. On evaporating the solvent, a slightly coloured oily residue is obtained which is chromatographed on silica, using $CHCl_3$ as eluent.

The fractions containing the product are added together and evaporated to dryness. The product obtained is in the form of a very dense colourless oil.

$[\alpha]_{25}^{589} = -27.2°$ (C = 1.0 in $CHCl_3$)

Chromatographic analysis (t.l.c. and h.p.l.c.) shows no presence of impurities, and the $^1H$ n.m.r. spectrum confirms the molecular structure.

Synthesis of (R,S)-malonyl-(2-benzyl)-alanyl-(4-benzyloxy)-proline methyl ester. (R,S)-mPhe-Ala-Hyp(OBz)-OMe 1.0 equivalent of Bu$^t$O-(R,S)-mPhe-Ala-Hyp(OBz)-OMe are dissolved in a 4.5N HCl solution in EtOAc. Having checked the disappearance of the starting substance, the solvent is evaporated to dryness. The product is obtained in the form of a very dense colourless oil. Chromatographic analysis (t.l.c. and h.p.l.c.) shows no presence of impurities, and the $^1H$ n.m.r. spectrum confirms the molecular structure.

Synthesis of gem-pyroglutamyl-D-lysyl-(N$^{\epsilon\text{-trifluoroacetyl}}$)-(R,S)-malonyl-(2-benzyl)-alanyl-(4-benzyloxy)-proline ester. gGlp-DLys-(N$^{\epsilon\text{-}TFA}$)-(R,S)mPhe-Ala-Hyp-(OBz)-OMe 1.0 equivalent of (R,S)mPhe-Ala-Hyp-(OBz)-OMe are dissolved in DMF, and 1.1 equivalents of gGlp-D-Lys-(N$^{\epsilon\text{-}TFA}$).HCl (obtained by removing the tert.butyloxycarbonyl from gGlp-Lys-(N$^{\epsilon\text{-}TFA}$)-Boc with 4.5N HCl in EtOAc) and 1.1 equivalents of DCC are added to the solution cooled to 0° C. and under strong agitation. The ice bath is removed after one hour, and the reaction mixture is left under agitation for a further 2.5 hours. Having checked the disappearance of the (R,S)mPhe-Ala-Hyp-(OBz)-OMe, the DCU precipitate is filtered off and washed with DFM. The solution and the DFM used for the washing are added together and evaporated to dryness under reduced pressure. The residue is taken up in THF, and after remaining at −20° C. for 2 hours is refiltered and evaporated to dryness. It is taken up in EtOAc and extracted with 5% sodium bicarbonate and water. The solvent is evaporated, and the residue is triturated with ethyl ether, filtered and dried.

M.P. = 163°-168° C. (dec.); $[\alpha]_{25}^{589} = -25°$ C. (c = 1.3 in $H_2O$)

Chromatographic analysis (t.l.c. and h.p.l.c.) shows no trace of impurities, and the $^1H$ n.m.r. spectrum confirms the molecular structure.

Synthesis of gem-pyroglutamyl-D-lysyl-(R,S)malonyl-(2-benzyl)-alanyl-(4-benzyloxy)-proline. gGlp-D-Lys-(R,S)mPhe-Ala-Hyp(OBz)

1.0 equivalent of gGlp-D-Lys-(N$^\epsilon$-TFA)-(R,S)mPhe-Ala-Hyp-(OBz)-OMe are dissolved in MeOH, and 5 equivalents of an aqueous solution of NaOH are added to the solution cooled to 0° C. and under strong agitation. After 4 hours, having checked the disappearance of the starting substance, concentrated HCl is added until neutrality, and the reaction mixture is evaporated to dryness after diluting with water. The residue is taken up in water and lyophilised. The product is isolated by high pressure preparative liquid chromatography with the stationary phase constituted by Lichroprep ® RP-18, 25-40μ (Merck), using 0.1% TFA and 38% MeCN in water as eluent. The fractions containing the product are added together, the MeCN is evaporated, and the required product obtained by lyophilisation. Chromatographic analysis shows no presence of impurities, and the $^1$H n.m.r. spectrum confirms the molecular structure.

Synthesis of
gem-pyroglutamyl-D-lysyl-(R,S)-malonyl-(2-benzyl)-alanyl-(4-allo-thiophenyl)-proline.
gGlp-D-Lys-(R,S)mPhe-Ala-Pro(4-allo-SPh)

Synthesis of
tert.butyloxycarbonyl-alanyl-(4-allo-thiophenyl)-proline methyl ester. Boc-Ala-Pro-(4-allo-SPh)-OMe 1.1 equivalents of Boc-Ala are dissolved in CH$_2$Cl$_2$, and 1.2 equivalents of HOBt dissolved in DMF and 1.1 equivalents of DCC dissolved in CH$_2$Cl$_2$ are added to the solution cooled to 0° C. and under strong agitation.

The ice bath is removed after 20 minutes. After 30 minutes, a solution of 1.0 equivalent of HCl.Pro(4-allo-SPh)-OMe [P. Zappelli et al., Italian Pat. No. 23335 (1981)] and 1.1 equivalents of NMM dissolved in CH$_2$Cl$_2$ is added. After 2 hours, having checked the disappearance of the HCl.Pro(4-allo-SPh)-OMe, the reaction mixture is filtered from the precipitated DCU and evaporated to dryness. The residue is taken up in ethyl acetate, the formed precipitate is again filtered off, and the organic solution extracted with 5% sodium bicarbonate, water, 0.1N HCl and water, and finally dried over magnesium sulphate. The product is obtained in the form of a colourless oil on evaporating the solvent.

Chromatographic analysis (t.l.c. and h.p.l.c.) shows no presence of impurities, and the $^1$H n.m.r. spectrum confirms the molecular structure.

Synthesis of the tert.butyl ester of
(R,S)-malonyl-(2-benzyl)-alanyl-(4-allo-thiophenyl)-proline methyl ester.
tBu$^t$O-(R,S)-mPhe-Ala-Pro-(4-allo-SPh)-OMe 1.1 equivalents of BuO$^t$(R,S)mPhe are dissolved in CH$_2$Cl$_2$, and 1.1 equivalents of HOBt dissolved in DMF and 1.1 equivalents of DCC dissolved in CH$_2$Cl$_2$ are added to the solution cooled to 0° C. and under strong agitation.

The ice bath is removed after 30 minutes, and the mixture left under agitation for a further 30 minutes at ambient temperature. 1.1 equivalents of HCl.Ala-Pro-(4-allo-SPh)-OMe (obtained by removing the tert.butyloxycarbonyl from Boc-Ala-Pro(4-allo-SPh)-OMe with 4.5N HCl in EtOAc) and 1.1 equivalents of NMM in CH$_2$Cl$_2$ are added.

After 2 hours, having checked the disappearance of the Bu$^t$OmPhe, the reaction mixture is filtered and evaporated to dryness. The oily residue is taken up in EtOAc and extracted with 5% sodium bicarbonate, water, 0.1N HCl and water. The organic solution is dried over magnesium sulphate and the solvent evaporated to dryness. The oily residue is chromatographed on silica, using CHCl$_3$ as eluent. The fractions containing the product are added together and evaporated. The product obtained is in the form of a very dense colourless oil. Chromatographic analysis (t.l.c. and h.p.l.c.) shows no presence of impurities, and the $^1$H n.m.r. spectrum confirms the molecular structure.

Synthesis of
(R,S)-malonyl-(2-benzyl)-alanyl-(4-allo-thiophenyl)-proline methyl ester.
(R,S)-mPhe-Ala-Pro-(4-allo-SPh)-OMe 1.0 equivalent of Bu$^t$O-(R,S)-mPhe-Ala-Pro-(4-allo-SPh)-OMe are dissolved in a 4.5N HCl solution in EtOAc.

After checking the disappearance of the starting substance, the reaction mixture is evaporated to dryness. The product is obtained as a very dense colourless oil.

Chromatographic analysis (t.l.c. and h.p.l.c.) shows no presence of impurities, and the $^1$H n.m.r. spectrum confirms the molecular structure.

Synthesis of
gem-pyroglutamyl-D-lysyl-(N$^\epsilon$-trifluoroacetyl)-(R,S)-malonyl-(2-benzyl)-alanyl-(4-allo-thiophenyl)-proline methyl ester.
gGlp-DLys(N$^\epsilon$-TFA)-(R,S)-mPhe-Ala-Pro-(4-allo-SPh)-OMe 1.0 equivalent of (R,S)-mPhe-Ala-Pro-(4-allo-SPh)-OMe are dissolved in DMF, and 1.1 equivalents of gGlp-DLys-(N$^\epsilon$-TFA).HCl, 1.1 equivalents of NMM, 1.2 equivalents of HOBt and finally 1.1 equivalents of DCC are added to the solution cooled to 0° C. and under strong agitation. The ice bath is removed after one hour. After a further 2.5 hours, having checked the disappearance of the (R,S)-mPhe-Ala-Pro-(4-allo-SPh)-OMe, the solution is filtered and the filtrate evaporated to dryness. The residue is taken up in THF, and after remaining at −20° C. for 2 hours is filtered and the filtrate evaporated to dryness. The residue is triturated with Et$_2$O, filtered and dried. Chromatographic analysis (t.l.c. and h.p.l.c.) shows no presence of impurities, and the $^1$H n.m.r. spectrum confirms the molecular structure.

M.P.=97°-101° C.
[α]$_{25}^{589}$=−6.2° (c=1.0 in MeOH)

Synthesis of
gem-pyroglutamyl-D-lysyl-(R,S)-malonyl-(2-benzyl)-alanyl-(4-allo-thiophenyl)-proline methyl ester.
gGlp-DLys-(R,S)-mPhe-Ala-Pro-(4-allo-SPh)

1.0 equivalent of gGlp-DLys-(N$^\epsilon$-TFZ)-(R,S)-mPhe-Ala-Pro(4-allo-SPh) are dissolved in a MeOH/pyridine (1:1 v/v) mixture, and 5 equivalents of MeOH in aqueous solution are added to the solution cooled to 0° C. and under strong agitation. After 4 hours, and having checked the disappearance of the starting substance, 3 equivalents of HCl in aqueous solution are added. The reaction mixture is evaporated to dryness after diluting with water.

The residue is taken up in water and lyophilised. The product is isolated by high pressure preparative liquid chromatography, the stationary phase being constituted by Lichroprep ® RP 18, 15–40μ (Merck), and using TFA 0.1%-MeCN 29% in water as eluent. The fractions containing the product are added together, the MeCN is evaporated, and the required product obtained by lyophilisation.

Chromatographic analysis (t.l.c. and h.p.l.c.) shows no presence of impurities, and the $^1$H n.m.r. spectrum confirms the molecular structure.

M.P.=165°-169° C.
[α]$_{25}^{589}$=24.0 (c=1.1 in H$_2$O)

Synthesis of pyroglutamyl-lysyl-phenylalanyl-alanyl-(4-benzyloxy)-proline. Glp-Lys-Phe-Ala-Hyp(OBz)

Synthesis of tert.butyloxycarbonyl-phenylalanyl-alanyl-(4-benzyloxy)-proline methyl ester. Boc-Phe-Ala-Hyp-(OBz)OMe 1.1 equivalents of Boc-Phe are dissolved in $CH_2Cl_2$, and 1.2 equivalents of HOBt dissolved in DMF and 1.1 equivalents of DCC dissolved in $CH_2Cl_2$ are added to the solution cooled to 0° C. and under strong agitation. The mixture is left under agitation for 30 minutes at 0° C. and for a further 30 minutes at ambient temperature. A solution of 1.0 equivalent of HCl.Ala-Hyp(OBz)OMe and 1.0 equivalent of NMM in $CH_2Cl_2$ is then added.

After 2 hours, and having checked the disappearance of the HCl.Ala-Hyp(OBz)OMe, the reaction mixture is filtered from the DCU precipitate and evaporated to dryness.

The residue is taken up in EtOAc and extracted with 5% sodium bicarbonate, water, 0.1N HCl and water. The organic solution is dried over magnesium sulphate.

The solvent is then evaporated, and the solid residue, dissolved in EtOAc, is crystallised by adding petroleum ether.

M.P. = 136° C.

$[\alpha]_{25}^{589} = -45.0$ (c = 2.0 in MeOH)

Chromatographic analysis (t.l.c. and h.p.l.c.) shows no trace of impurities, and the $^1H$ n.m.r. spectrum confirms the molecular structure.

Synthesis of tert.butyloxycarbonyl-lysyl-($N^\epsilon$-trifluoroacetyl)-phenylalanyl-alanyl-(4-benzyloxy)-proline methyl ester. Boc-Lys-$N^\epsilon$-TFA)-Phe-Ala-Hyp(OBz)OMe 1.2 equivalents of HOBt dissolved in DMF and 1.1 equivalents of DCC dissolved in $CH_2Cl_2$ are added to 1.0 equivalent of Boc-Lys($N^\epsilon$-TFA) dissolved in $CH_2Cl_2$, at 0° C. and under strong agitation. The mixture is left under agitation for 30 minutes at 0° C. and for a further 30 minutes at ambient temperature. A solution of 1.0 equivalent of HCl.Phe-Ala-Hyp-(OBz)OMe (obtained by removing the tert. butyloxycarbonyl from Boc-Phe-Ala-Hyp-(OBz)OMe with 4.5N HCl in EtOAc) in $CH_2Cl_2$ is then added. After one hour, and having checked the disappearance of HCl.Phe-Ala-Hyp-(OBz)OMe, the precipitated DCU is filtered off and the solution evaporated to dryness. The solid residue is washed firstly with EtOAc and then with 5% sodium bicarbonate and water. The product is filtered and dried by $P_2O_5$. M.P. = 186°-187° C.; $[\alpha]_{25}^{581} = 45.0°$ (C = 2.0 in MeOH).

Chromatographic analysis (t.l.c. and h.p.l.c.) shows no presence of impurities, and the $^1H$ n.m.r. spectrum confirms the molecular structure.

Synthesis of pyroglutamyl-lysyl-($N^\epsilon$-trifluoroacetyl)-phenylalanyl-alanyl-(4-benzyloxy)-proline methyl ester. Glp-Lys-($N^\epsilon$-TFA)-Phe-Ala-Hyp(OBz)OMe 1.1 equivalents of Glp-OPCP are dissolved in anhydrous DMF, and 1.0 equivalent of HOBt and 1.0 equivalent of HCl.Lys-($N^\epsilon$-TFA)-Phe-Ala-Hyp-(OBz)OMe (obtained by removing the tert.butyloxycarbonyl from Boc-Lys-($N^\epsilon$-TFA)-Phe-Ala-Hyp-(4-OBz)OMe with 4.5N HCl in EtOAc) are added to the solution cooled to 0° C. and under strong agitation. The mixture is left under agitation at 4° C. for 16 hours, and the reaction is then suspended by evaporating the solvent.

The solid residue is washed with EtOAc, and after drying is again washed with 5% sodium bicarbonate, water, 0.1N HCl and water. The product is filtered and dried in the presence of $P_2O_5$.

M.P. = 195°-200° C. (dec.)

$[\alpha]_{25}^{589} = -50.0°$ (C = 1.0 in MeOH)

Chromatographic analysis (t.l.c. and h.p.l.c.) shows no presence of impurities, and the $^1H$ n.m.r. spectrum confirms the molecular structure.

Synthesis of pyroglutamyl-lysyl-phenylalanyl-alanyl-(4-benzyloxy)-proline. Glp-Lys-Phe-Ala-Hyp(OBz)

1.0 equivalent of Glp-Lys-($N^\epsilon$-TFA)-Phe-Ala-Hyp-(OBz)OMe are dissolved in a MeOH/pyridine (1:1 v/v) mixture, and 6 equivalents of NaOH in aqueous solution are added to the solution. After diluting with water, the reaction mixture is evaporated to dryness, the residue taken up in water and lyophilised. The product is isolated by high pressure preparative chromatography with the stationary phase constituted by Lichroprep ® RP-18, 25–41μ (Merck), using 0.1% TFA-35% MeCN in water as eluent. The fractions containing the product are added together, the MeCN is evaporated, and the required product obtained by lyophilisation.

M.P. = 180°-185° C. (dec.)

$[\alpha]_{25}^{589} = 57.0°$ (C = 1.0 in $H_2O$)

Chromatographic analysis (t.l.c. and h.p.l.c.) shows no presence of impurities, and the $^1H$ n.m.r. spectrum confirms the molecular structure.

Synthesis of pyroglutamyl-lysyl-phenylalanyl-alanyl-(4-allo-thiophenyl)-proline. Boc-Phe-Ala-Pro-(4-allo-SPh)OMe 1.1 equivalents of Boc-Phe are dissolved in $CH_2Cl_2$, and 1.2 equivalents of HOBt dissolved in DMF and 1.1 equivalents of DCC dissolved in $CH_2Cl_2$ added to the solution cooled to 0° C. and under strong agitation. The mixture is left under agitation for 30 minutes at 0° C. and for a further 30 minutes at ambient temperature. A solution of 1.0 equivalent of HCl.Ala-Pro-(4-SPh)-OMe and 1.0 equivalent of NMM in $CH_2Cl_2$ is then added.

After 2 hours, and having checked the disappearance of HCl.Ala-Pro-(4-SPh)-OMe, the reaction mixture is filtered of the precipitated DCU and evaporated to dryness. The residue is taken up in EtOAc and extracted with 5% sodium bicarbonate, water, 0.1N HCl and water. The solution is then evaporated and the solid residue, dissolved in EtOAc, is crystallised by adding petroleum ether.

M.P. = 149°-150° C.; $[\alpha]_{25}^{589} = -25.4°$ (C = 1.0 in MeOH)

Chromatographic analysis (t.l.c. and h.p.l.c.) shows no presence of impurities, and the $^1H$ n.m.r. spectrum confirms the molecular structure.

Synthesis of tert.butyloxycarbonyl-lysyl-($N^\epsilon$-trifluoroacetyl)-phenylalanyl-alanyl-(4-allo-thiophenyl)-proline methyl ester. Boc-Lys-($N^\epsilon$-TFA)-Phe-Ala-Pro-(4-allo-SPh)-OMe 1.2 equivalents of HOBt dissolved in DMF and 1.1 equivalents of DCC dissolved in $CH_2Cl_2$ are added at 0°

C. and under strong agitation to 1.0 equivalent of Boc-Lys-(N^ε-TFA) dissolved in CH₂Cl₂.

The mixture is left under agitation for 30 minutes at 0° C. and for a further 30 minutes at ambient temperature. A solution of 1.0 equivalent of NMM and of HCl.Phe-Ala-Pro-(4-allo-SPh)-OMe (obtained by removing the tert.butyloxycarbonyl from Boc-Phe-Ala-Pro-(4-allo-SPh) with 4.5N HCl in EtOAc) in CH₂Cl₂ is then added. After about one hour, and having checked the disappearance of the HCl.Phe-Ala-Pro-(4-allo-SPh)OMe, the precipitated DCU is filtered off and the solution evaporated to dryness.

The solid residue is washed with EtOAc and then with 5% sodium bicarbonate and water. The product is isolated by filtration and dried in the presence of P₂O₅.

M.P. = 178°–179° C.

$[\alpha]_{25}^{587} = 30.0°$ (C = 1.05 in MeOH)

Chromatographic analysis (t.l.c. and h.p.l.c.) shows no presence of impurities, and the ¹H n.m.r. spectrum confirms the molecular structure.

Synthesis of pyroglutamyl-lysyl-(N^ε-trifluoroacetyl)-phenylalanyl-alanyl-(4-allo-thiophenyl)-proline methyl ester.

Glp-Lys-(N^ε-TFA)-Phe-Ala-Pro-(4-allo-SPh)OMe 1.0 equivalent of Glp-OPCP are dissolved in anhydrous DMF, and 1.0 equivalent of HOBt, 1.0 equivalent of NMM and 1.0 equivalent of HCl.Lys-(N^ε-TFA)-Phe-Ala-Pro(4-allo-SPh)OMe [obtained by removing the tert.butyloxycarbonyl from Boc-Lys-(N^ε-TFA)-Phe-Ala-Pro-(4-allo-SPh)OMe with 4.5N HCl in EtOAc] are added to the solution cooled to 0° C. and under strong agitation.

The mixture is left under agitation at 4° C. for 16 hours, and the reaction is suspended by evaporating the solvent. The solid residue is washed with EtOAc, and after drying is further washed with 5% sodium bicarbonate, water, 0.1N HCl and water. The product is filtered, washed with water and dried in the presence of P₂O₅.

M.P. = 210°–214° C. (dec.)

$[\alpha]_{25}^{589} = -35.0°$ (C = 1.0 in MeOH)

Chromatographic analysis (t.l.c. and h.p.l.c.) shows no presence of impurities, and the ¹H n.m.r. spectrum confirms the molecular structure.

Synthesis of pyroglutamyl-lysyl-phenylalanyl-proline-(4-allo-thiophenyl). Glp-Lys-Phe-Ala-Pro-(4-allo-SPh)

1.0 equivalent of Glp-Lys-(N^ε-TFA)-Phe-Ala-Pro(4-allo-SPh)-OMe are dissolved in a MeOH/pyridine (1:1 v/v) mixture, and 6 equivalents of NaOH in aqueous solution are added to the solution.

After one hour, and having checked the disappearance of the starting substance, 6 equivalents of HCl in aqueous solution are added. After diluting with water, the reaction mixture is evaporated to dryness. The residue is taken up in water and lyophilised. The product is isolated by high pressure preparative chromatography, with the stationary phase constituted by Lichroprep® RP-18, 25–40μ (Merck), using 0.1% TFA-32% MeCN in water as eluent. The fractions containing the product are added together, the MeCN is evaporated, and the required product obtained by lyophilisation.

M.P. = 148°–150° C. (dec.)

$[\alpha]_{25}^{589} = -32.0°$ (C = 1.0 in H O)

Chromatographic analysis shows no presence of impurities, and the ¹H n.m.r. spectrum confirms the molecular structure.

We claim:

1. The product

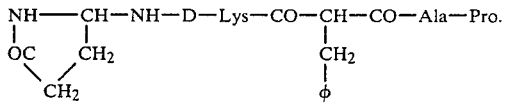

2. The product

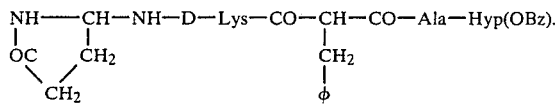

3. The product

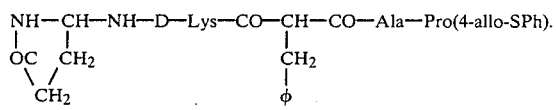

4. The product

Glp-Lys-Phe-Ala-Hyp-(OBz).

5. The product

Glp-Lys-Phe-Ala-Pro(4-allo-SPh).

* * * * *